United States Patent
Khachik

(10) Patent No.: US 9,725,411 B2
(45) Date of Patent: Aug. 8, 2017

(54) PROCESS FOR A DIRECT ONE-POT TRANSFORMATION OF LUTEIN TO β-CRYPTOXANTHIN VIA ITS ACETATE ESTER

(71) Applicant: University of Maryland, College Park, College Park, MD (US)

(72) Inventor: Frederick Khachik, Rockville, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 14/891,499

(22) PCT Filed: May 16, 2014

(86) PCT No.: PCT/US2014/038356
§ 371 (c)(1),
(2) Date: Nov. 16, 2015

(87) PCT Pub. No.: WO2014/186683
PCT Pub. Date: Nov. 20, 2014

(65) Prior Publication Data
US 2016/0115122 A1    Apr. 28, 2016

Related U.S. Application Data

(60) Provisional application No. 61/941,782, filed on Feb. 19, 2014, provisional application No. 61/824,130, filed on May 16, 2013.

(51) Int. Cl.
*C07C 403/24*    (2006.01)
(52) U.S. Cl.
CPC ........ *C07C 403/24* (2013.01); *C07C 2101/16* (2013.01)

(58) Field of Classification Search
CPC .................................................. C07C 403/24
See application file for complete search history.

(56) References Cited

U.S. PATENT DOCUMENTS

| | | | |
|---|---|---|---|
| 6,911,564 B2 | 6/2005 | Khachik | |
| 7,115,786 B2 | 10/2006 | Khachik | |
| 8,097,762 B2 | 1/2012 | Khachik et al. | |
| 2003/0220525 A1 | 11/2003 | Khachik | |
| 2006/0088631 A1 | 4/2006 | Khachik et al. | |

FOREIGN PATENT DOCUMENTS

JP    2000-136181    5/2000

OTHER PUBLICATIONS

Philip, T. et al., Nautr eof Lutein Acylation in Marigold (Tagetes erecta) Flowers, 1975, Journal of Food Science, vol. 40. pp. 1089-1090.*
Espacenet English language abstract for Japanese Patent Publication No. 2000-136181, 2 pages (2000).
International Search Report for International Application No. PCT/US14/38356, United States Patent and Trademark Office, United States, mailed on Sep. 12, 2014.

* cited by examiner

*Primary Examiner* — Yate K Cutliff
(74) *Attorney, Agent, or Firm* — Sterne, Kessler, Goldstein & Fox P.L.L.C.

(57) ABSTRACT

The present invention relates to a process for converting commercially available lutein and/or lutein esters from extracts of marigold flower petals to (3R)-β-cryptoxanthin (major) and (3R,6'R)-α-cryptoxanthin (minor) in ratios ranging from 95:5 to 98:2 in a one-pot reaction at room temperature. Because the entire process can be carried out by employing safe and environmentally friendly food-grade reagents, the resulting mixture of these carotenoids is suitable for human consumption as a dietary supplement.

14 Claims, No Drawings

PROCESS FOR A DIRECT ONE-POT TRANSFORMATION OF LUTEIN TO β-CRYPTOXANTHIN VIA ITS ACETATE ESTER

BACKGROUND OF THE INVENTION

Field of the Invention

The present invention is in the field of organic chemistry. The present invention relates to an efficient process for the direct transformation of commercially available (3R,3'R,6'R)-lutein or unsaponified extracts of lutein from marigold flower petals containing 4-5% (3R,3'R)-zeaxanthin to (3R)-β-cryptoxanthin in 97% purity via (3R)-β-cryptoxanthin esters under very mild reaction conditions.

Related Art

The present invention is a unique modification of three earlier processes that have been reported for the conversion of commercially available (3R,3'R,6'R)-lutein to a mixture of (3R)-β-cryptoxanthin and (3R,6'R)-α-cryptoxanthin. The uniqueness of the present invention is based on the fact that several chemical reactions that allow the transformation of (3R,3R,6'R)-lutein to (3R)-β-cryptoxanthin have all been carried out in, a single step in a one pot reaction at room temperature. In, addition, the resulting (3R)-β-cryptoxanthin is in excess of 97% pure and is not accompanied by any significant amount of (3R,6'R)-α-cryptoxanthin. Further, the reaction conditions for this transformation can be adjusted to obtain any ratios of (3R)-β-cryptoxanthin to (3R,6'R)-α-cryptoxanthin.

The first process for the conversion of lutein to a mixture of (3R)-β-cryptoxanthin and (3R,6'R)-α-cryptoxanthin, was reported by Khachik in U.S. Pat. No. 6,911,564. This process involved conversion of lutein (1) containing approximately 5-7% (3R,3'R)-zeaxanthin (2) to a mixture of (3R)-β-cryptoxanthin (6) and (3R,6'R)-α-cryptoxanthin (7) via (3R,6'R)-anhydrolutein I ((3R,6'R)-3-Hydroxy-3',4'-didehydro-β,γ-carotene) (3), (3R,6'R)-2',3'-anhydrolutein II ((3R,6'R)-3-Hydroxy-2',3'-didehydro-β,ε-carotenene) (4), and (3R)-3',4'-anhydrolutein III ((3R)-3-Hydroxy-3',4'-didehydro-β,β-carotene) (5) in one synthetic step by allylic deoxygenation with a strong acid and a hydride ion donor. The chemical structures of these carotenoids are shown in Scheme 1.

SCHEME 1

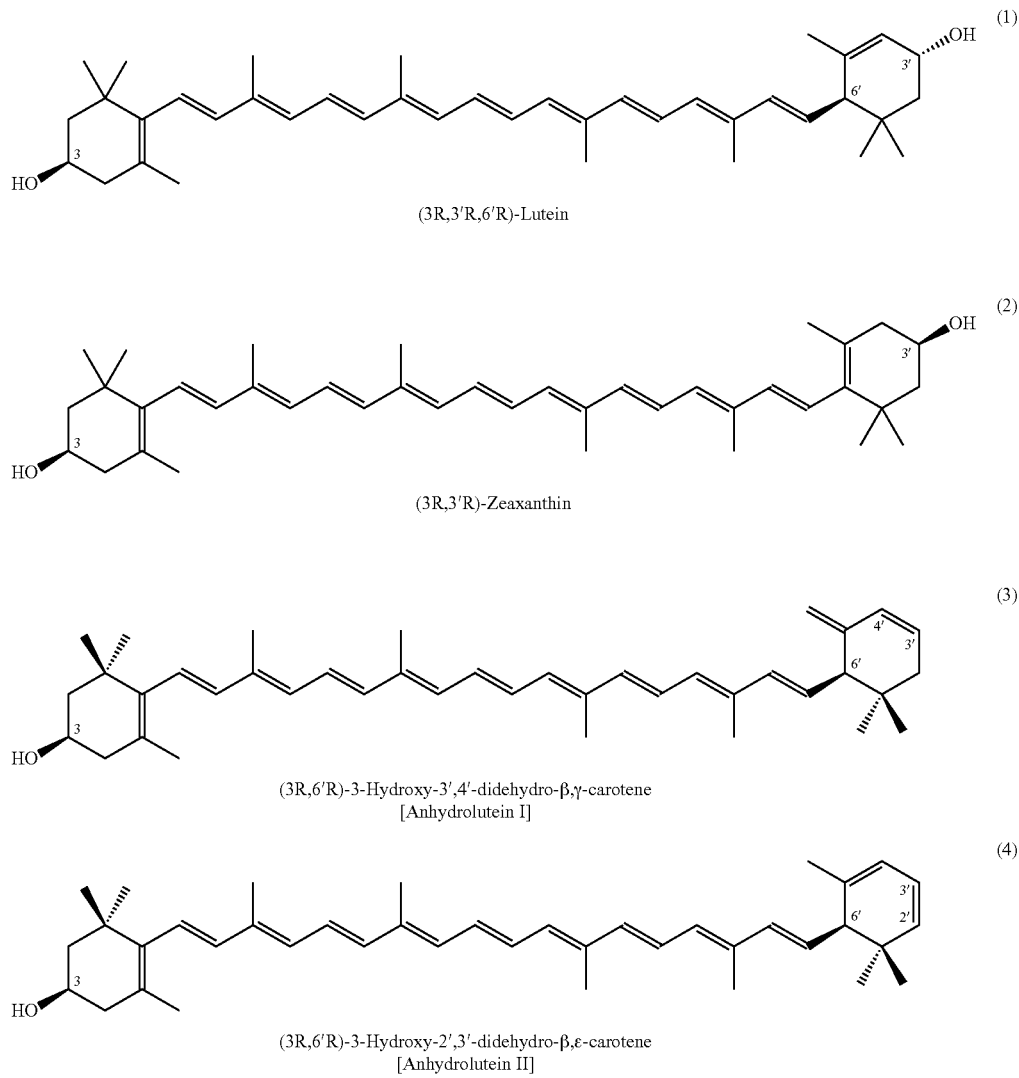

(3R,3'R,6'R)-Lutein (1)

(3R,3'R)-Zeaxanthin (2)

(3R,6'R)-3-Hydroxy-3',4'-didehydro-β,γ-carotene
[Anhydrolutein I] (3)

(3R,6'R)-3-Hydroxy-2',3'-didehydro-β,ε-carotene
[Anhydrolutein II] (4)

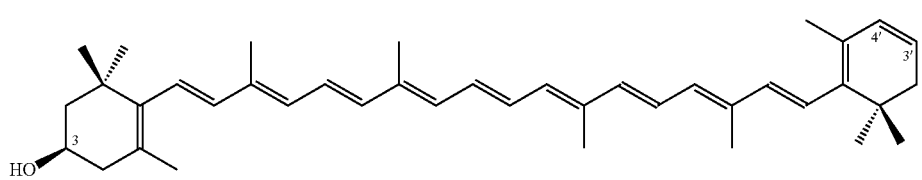

(3R)-3-Hydroxy-3',4'-didehydro-β,β-carotene
[3',4'-Anhydrolutein III]

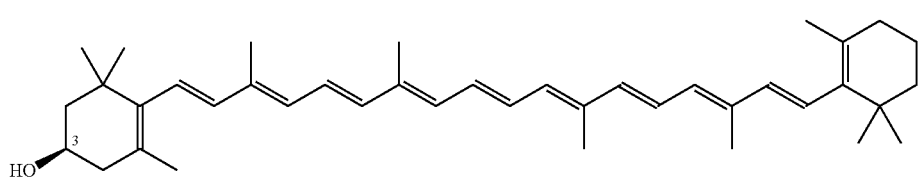

(3R)-β-Cryptoxanthin

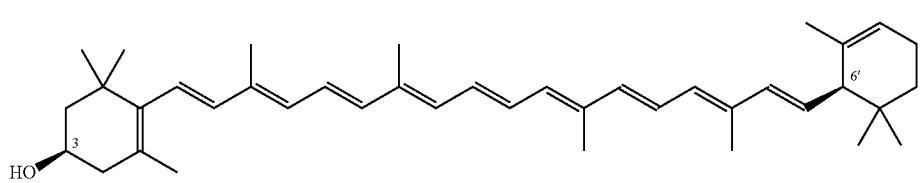

(3R,6'R)-α-Cryptoxanthin

The chemical structures of (3R,3'R,6'R)-lutein, (3R,3'R)-zeaxanthin, anhydroluteins I, II, and III, (3R)-β-cryptoxanthin, and (3R,6'R)-α-cryptoxanthin. The systematic names of carotenoids are shown below their structures.

U.S. Pat. No. 6,911,564 also described a two-step alternative process. The first step converted lutein to a mixture of anhydroluteins I, II, and III at room temperature in the presence of an acid and in the second step, the isolated anhydroluteins were converted to (3R)-β-cryptoxanthin and (3R,6'R)-α-cryptoxanthin with a strong acid and a hydride ion donor.

As described in U.S. Pat. No. 6,911,564, the acid-catalyzed dehydration of lutein in a homogenous phase in a variety of solvents such as ethers (tetrahydrofuran, tert-butyl methyl ether), chlorinated solvents (dichloromethane, chloroform, 1,2-dichloroethane), acetone, and toluene at ambient temperature led to the formation of considerable amount of Z(cis)-isomers of anhydroluteins. In addition, under the conditions disclosed in U.S. Pat. No. 6,911,564, anhydrolutein I was the major product and anhydroluteins II and III were the minor products. Because anhydrolutein III was the precursor to (3R)-β-cryptoxanthin in the ionic hydrogenation step, a higher ratio of this carotenoid relative to anhydroluteins I and II was preferred. Therefore, according to U.S. Pat. No. 6,911,564 a mixture of (3R)-β-cryptoxanthin and (3R,6'R)-α-cryptoxanthin could be obtained in the ratio of 3:1.

In a second process described in U.S. Pat. No. 7,115,786, Khachik reported a modified two-step process for the dehydration of (3R,3'R,6'R)-lutein that significantly improved the ratio of anhydrolutein III (5) to anhydroluteins I (3) and II (4) and allowed the transformation of these lutein dehydration products to a mixture of (3R)-β-cryptoxanthin (6) and (3R,6'R)-α-cryptoxanthin (7) in the ratio of 3:1. In the first step according to U.S. Pat. No. 7,115,786, lutein was allowed to react with an alcohol, used as solvent, in the presence of a catalytic amount of an acid between 45-50° C. to give the corresponding 3'-alkyl ethers of lutein. Water and additional acid were then added to the mixture and the temperature was raised to 78-88° C. to convert the resulting lutein 3'-alkyl ethers to a mixture, of anhydroluteins I, II, and III, quantitatively (Scheme 2). At the beginning of this transformation, anhydrolutein I was the major product and anhydrolutein II and III were the minor products. As heating continued at 78-88° C., anhydroluteins I and II were partially isomerized to anhydrolutein III within 7-20 hours depending on the nature of the alcohol.

SCHEME 2

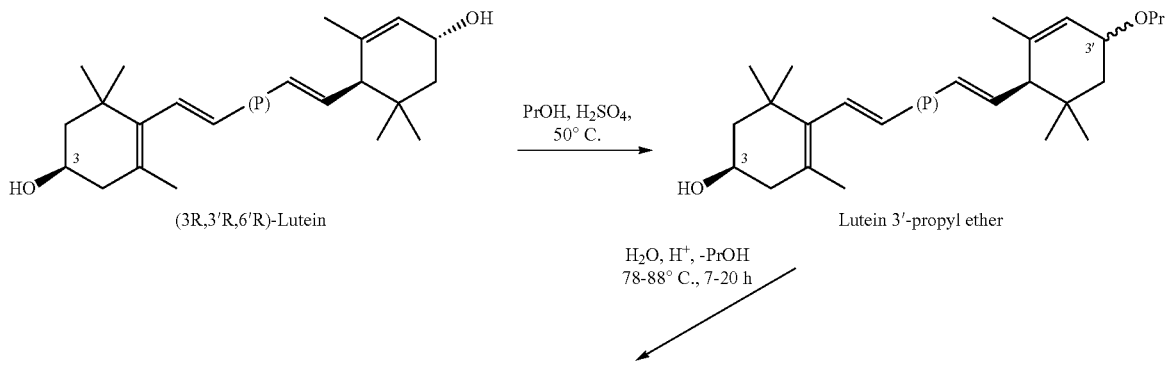

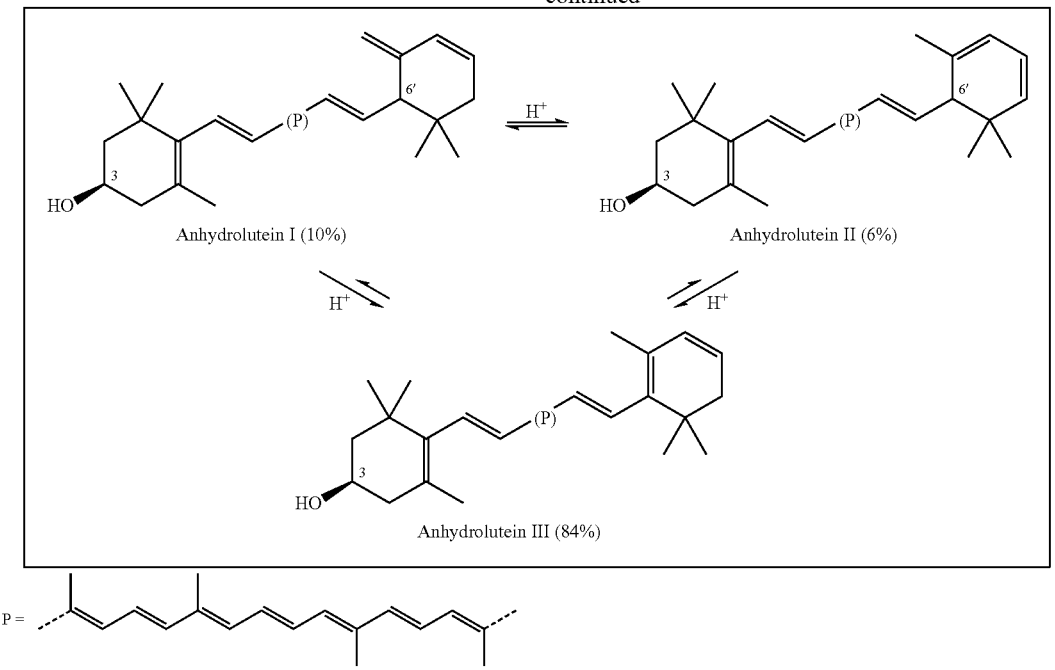

Dehydration of lutein to anhydrolutein III according to U.S. Pat. No. 7,115,786.

In the second step of U.S. Pat. No. 7,115,786, the resulting product, rich in anhydrolutein III, was allowed to react with about 1.3 equivalents of a hydride donor and about 3.5-4 equivalents of a strong organic acid in a chlorinated solvent at ambient temperature for about 1-5 hours to give a mixture of E/Z-(3R)-β-cryptoxanthin, E/Z-(3R,6'R)-α-cryptoxanthin, and minor quantities of unreacted anhydroluteins I and II.

According to a third process disclosed in U.S. Pat. No. 8,097,762, Khachik et al. developed an alternative route to the second step of U.S. Pat. No. 7,115,786 for making (3R)-β-cryptoxanthin and (3R,6'R)-α-cryptoxanthin from anhydroluteins that eliminated the use of chlorinated solvents and reagents such as trifluoroacetic acid, and hydride donors such as borane-amine complex. This was accomplished by heterogeneous or homogeneous regioselective catalytic hydrogenation of anhydroluteins as shown in Scheme 3. In addition, this process also employed a mixture of esterified luteins as the starting material to prepare anhydroluteins that were then transformed to (3R)-β-cryptoxanthin and (3R,6'R)-α-cryptoxanthin by regioselective catalytic hydrogenation. However, because strongly acidic conditions and high temperature were used, this transformation was accompanied by significant losses of the desired carotenoids.

SCHEME 3

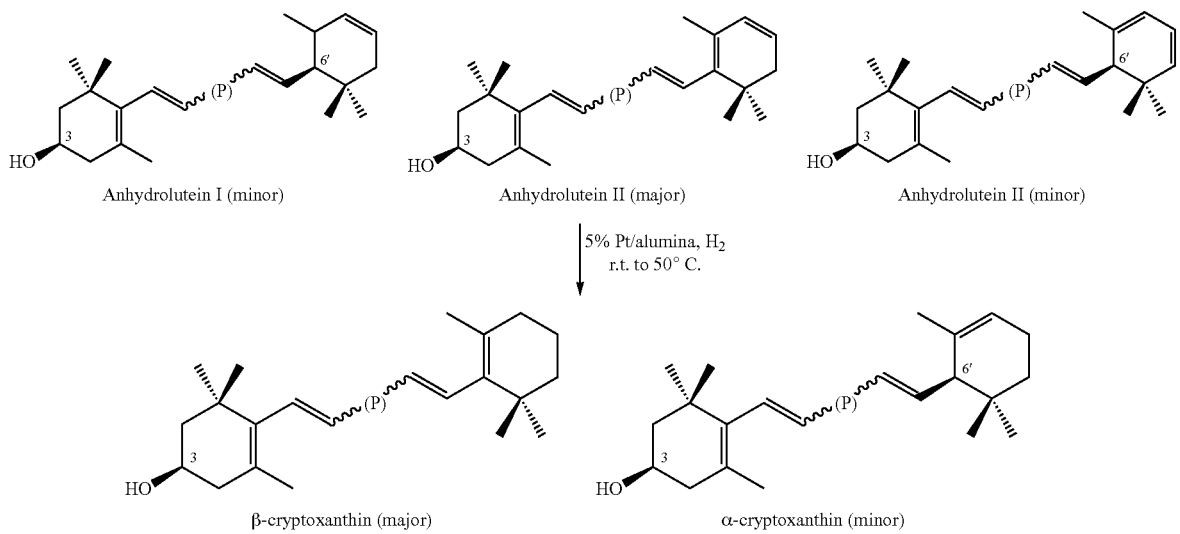

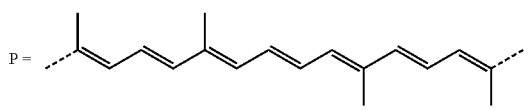

Catalytic hydrogenation of anhydroluteins I, II, and III to (3R)-β-cryptoxanthin and (3R 6'R)-α-cryptoxanthin according to U.S. Pat. No. 8,097,762.

In all three processes, (3R)-β-cryptoxanthin is accompanied by significant amounts of (3R,6'R)-α-cryptoxanthin; therefore, a new and simplified methodology is needed that allows the direct transformation of lutein or unsaponified extracts of lutein from marigold flowers to (3R)-β-cryptoxanthin as the sole product under very mild conditions.

SUMMARY OF THE INVENTION

In some embodiments, the present invention provides a process for the preparation of (3R)-β-cryptoxanthin acetate comprising reacting (3R,3'R,6'R)-lutein with concentrated mineral acid or a strong organic acid, a heterogeneous hydrogenation catalyst, an acylating ester, and hydrogen in one reaction to provide (3R)-β-cryptoxanthin acetate.

In some embodiments, the (3R 3'R,6'R)-lutein is purified by pretreatment with, a dilute solution of a mineral acid in an alcohol at a temperature between about 50° C. to about 60° C. to remove anthocyanins and degradation products of chlorophylls. In some embodiments, the alcohol is methanol, ethanol, 1-propanol, or 2-propanol.

In some embodiments, the process further comprises a solvent selected from the group consisting of acetone, tetrahydrofuran, a hydrocarbon solvent, and combinations thereof. In some embodiments, the hydrocarbon solvent is selected from the group consisting of pentane, hexane, and heptane.

In some embodiments, the acylating ester is selected from the group consisting of ethyl acetate, methyl acetate, isopropyl acetate, propyl acetate, and isopropenyl acetate.

In some embodiments, the present invention provides a process for the preparation of (3R)-β-cryptoxanthin, comprising saponifying the (3R)-β-cryptoxanthin acetate to provide (3R)-β-cryptoxanthin.

In some embodiments, the present invention provides a process for the preparation of (3R)-β-cryptoxanthin comprising transesterifying the (3R)-β-cryptoxanthin acetate with an alcohol in the same reaction vessel in the presence of the concentrated mineral acid or strong organic acid to provide (3R)-β-cryptoxanthin and the acyl ester of the alcohol. In some embodiments, the alcohol is a $C_2$-$C_5$ straight chain alkyl alcohol. In some embodiments, the $C_2$-$C_5$ straight chain alkyl alcohol is selected from the group consisting of ethanol, 1-propanol, 1-butanol, 2-butanol, 1-pentanol, 2-pentanol, 3-pentanol, and combinations thereof.

In some embodiments, the concentrated mineral acid or strong organic acid is selected from the group consisting of about 50% sulfuric acid, hydrochloric acid, phosphoric acid, trifluoroacetic acid, and benzenesulfonic acid.

In some embodiments, the heterogeneous hydrogenation catalyst is selected from the group consisting of platinum (Pt) supported on alumina (5%), Pt supported on activated carbon (5%), Pt supported on activated carbon (10%), palladium (Pd) supported on activated carbon (5%), Pd supported on activated carbon (10%), Pd supported on alumina (5%), Pd supported on alumina (10%), Pd supported on calcium carbonate (5%), Pd 3% on polyethyleneimine/$SiO_2$, rhodium (Rh) supported on alumina (5%), ruthenium supported on carbon, and ruthenium supported on alumina.

In some embodiments, the acylating ester is selected from the group consisting of ethyl acetate, methyl acetate, isopropyl acetate, propyl acetate, and isopropenyl acetate.

In some embodiments, the reacting is carried out at a temperature between about 23° C. to about 45° C.

In some embodiments, the saponifying is carried out in a mixture of potassium hydroxide or sodium hydroxide and an alcohol at a temperature between about 50° C. to about 70° C. In some embodiments, the alcohol is selected from the group consisting of methanol, ethanol, 1-propanol, and 2-propanol.

In some embodiments, the transesterifying is carried out in an alcohol in the presence of a catalytic amount of a mineral acid at a temperature between about 60° C. to about 80° C. In some embodiments, the mineral acid is selected from the group consisting of hydrochloric acid, sulfuric acid, and phosphoric acid.

In some embodiments, the (3R,3'R,6'R)-lutein is present in a composition comprising 4-5% (3R,3'R)-zeaxanthin.

In some embodiments, the present invention provides a process for the preparation of (E)-(3R)-β-cryptoxanthin comprising reacting the (3R)-β-cryptoxanthin in an alcohol with Pd(OAc)$_2$ at temperature between about 50° C. to about 70° C. for between about 2 to about 5 hours to provide (E)-(3R)-β-cryptoxanthin.

In some embodiments, the process further comprises isolating the (3R)-β-cryptoxanthin by crystallization from a mixture of acetone and an alcohol or ethyl acetate and an alcohol. In some embodiments, the alcohol is selected from the group consisting of methanol, ethanol, 1-propanol, and 2-propanol.

In some embodiments, the isolated (3R)-β-cryptoxanthin is at least 96% pure.

In some embodiments, the (3R,3'R,6'R)-lutein may be present as lutein fatty acid esters in a composition comprising 4-5% (3R,3'R)-zeaxanthin fatty acid esters. In some embodiments, the lutein fatty acid esters are selected from the group consisting of lutein dimyristate, lutein dipalmitate, and combinations thereof.

In some embodiments, the source of the lutein fatty acid esters is extracts of marigold flowers or marigold petal flowers.

In some embodiments, the lutein fatty acid esters are purified by pretreatment with a dilute solution of a mineral acid in an alcohol at a temperature between about 50° C. and about 60° C. to remove anthocyanins and degradation products of chlorophylls. In some embodiments, the mineral acid is selected from the group consisting of hydrochloric acid, sulfuric acid, and phosphoric acid.

In some embodiments, the present invention provides a process for the preparation of (3R)-β-cryptoxanthin comprising:

(a) reacting at room temperature a composition comprising (3R,3'R,6'R)-lutein and 4-5% (3R,3'R)-zeaxanthin with a mixture of about 50% sulfuric acid, platinum on alumina, ethyl acetate, and hydrogen in one reaction to give (3R)-β-cryptoxanthin acetate;

(b) isolating the (3R)-β-cryptoxanthin acetate;

(c) saponifying the (3R)-β-cryptoxanthin acetate at a temperature between about 50° C. to about 70° C. in a mixture of potassium hydroxide or sodium hydroxide and ethanol to provide (3R)-β-cryptoxanthin; or (c) transesterifying the (3R)-β-cryptoxanthin acetate at a temperature between about 60° C. to about 80° C. with an alcohol selected from the group consisting of methanol, ethanol, 1-propanol, and 2-propanol, and a mineral acid to give (3R)-β-cryptoxanthin; and (d) isolating the (3R)-β-cryptoxanthin by crystallization from acetone and an alcohol or ethyl acetate and an alcohol.

In some embodiments, the present invention provides a process for the preparation of (3R)-β-cryptoxanthin comprising:

(a) reacting at room temperature an extract of marigold flowers comprising (3R,3'R,6'R)-lutein fatty acid esters and 4-5% (3R,3'R)-zeaxanthin fatty acid esters with a mixture of about 50% sulfuric acid, platinum on alumina, ethyl acetate, and hydrogen in one reaction to provide (3R)-β-cryptoxanthin fatty acid esters;

(b) isolating the (3R)-β-cryptoxanthin fatty acid esters;

(c) saponifying the (3R)-β-cryptoxanthin fatty acid esters at a temperature between about 50° C. to about 70° C. in a mixture of potassium hydroxide or sodium hydroxide and ethanol to provide (3R)-β-cryptoxanthin; or (c) transesterifying the (3R)-β-cryptoxanthin fatty acid esters at a temperature between about 60° C. to about 80° C. with an alcohol selected from the group consisting of methanol, ethanol, 1-propanol, and 2-propanol, and a mineral acid to provide (3R)-β-cryptoxanthin; and (d) isolating the (3R)-β-cryptoxanthin by crystallization from acetone and an alcohol or ethyl acetate and an alcohol.

In some embodiments, the crystallization is from acetone and ethanol or ethyl acetate and ethanol.

In some embodiments, the isolated (3R)-β-cryptoxanthin is at least 96% pure.

DETAILED DESCRIPTION OF THE INVENTION

As used herein, the term "comprising" means including, made up of and composed of.

All numbers in this description indicating amounts, ratios of materials, physical properties of materials, and/or use are to be understood as modified by the word "about," except as otherwise explicitly indicated.

The term "about" as used herein includes the recited number±10%. Thus, "about ten" means 9 to 11.

(3R)-β-Cryptoxanthin is a rare food carotenoid that is not commercially available and exhibits vitamin A activity. According to the process of the present invention, commercially available lutein or lutein esters in an acylating solvent (acetates of various alcohols) is treated with a concentrated mineral acid or a strong organic acid, a heterogeneous hydrogenation catalyst, and hydrogen in one reaction to give (3R)-β-cryptoxanthin acetate or (3R)-β-cryptoxanthin fatty acid esters. In some embodiments, the heterogeneous catalyst is selected from transition elements of group VIII. In some embodiments, hydrogenation is carried out under an atmospheric pressure of hydrogen at room temperature. In some embodiments, the heterogeneous catalyst is Pt supported on alumina. Pt supported on carbon, Pd supported on alumina, Pd supported on carbon, Rh supported on alumina, or Rh supported on carbon. Among these catalysts. Pt supported on alumina in ethyl acetate provides the best yield of (3R)-β-cryptoxanthin. The most novel feature of this invention is the fact that the three reactions that lead to the formation of the desired product can all be carried out in one-pot at room temperature and under mild reaction conditions. The three reactions are: (1) dehydration of lutein or lutein fatty acid esters; (2) transesterification of the resulting anhydroluteins to anhydrolutein acetate or anhydrolutein fatty acid esters; and (3) regioselective catalytic hydrogenation of anhydrolutein esters to yield (3R)-β-cryptoxanthin acetate or (3R)-β-cryptoxanthin fatty acid esters. In the final step of this process, these carotenoid esters are either saponified or subjected to acid catalyzed transesterification to generate carotenoids. Another novel aspect of this invention is the fact that crude and impure marigold oleoresin containing lutein esters can be employed as starting material and is readily transformed to (3R)-β-cryptoxanthin at room temperature under mild reaction conditions. This significantly simplifies the large-scale production of (3R)-β-cryptoxanthin by an economically viable process.

To simplify the production of (3R)-β-cryptoxanthin (6) from lutein (1), attempts were made to combine the dehydration and heterogeneous catalytic hydrogenation steps into a one-pot reaction. However, the dehydration of lutein to anhydroluteins would have to be done at high temperature (78-88° C.) in order to increase the ratio of anhydrolutein III (5) to anhydrolutein I (3) and anhydrolutein II (4). In addition, the high temperature and high concentration of acid that were needed according to U.S. Pat. No. 7,115,786 were not compatible with the second step of this process that employed catalytic hydrogenation of anhydroluteins to (3R)-β-cryptoxanthin (6) and (3R,6'R)-α-cryptoxanthin (7). This is because the catalytic hydrogenation step had to be carried out at temperatures in the range of 25-40° C. Therefore, numerous attempts to combine the dehydration and catalytic hydrogenation steps failed to produce (3R)-β-cryptoxanthin (6) and (3R,6'R)-α-cryptoxanthin (7) as these carotenoids were either degraded of underwent excessive hydrogenation under the forementioned reaction conditions. Further, under these conditions, 6 was accompanied by significant, amounts of 7.

Therefore, the dehydration of lutein and regioselective heterogeneous catalytic hydrogenation of anhydrolutein had to be carried out under mild conditions and in solvents that would be acceptable in the food industry. This is because the ultimate goal was to develop a process for production of (3R)-β-cryptoxanthin in purities equal to or greater than 97% so that this carotenoid can be used as a nutritional supplement. While according to U.S. Pat. No. 6,911,564 lutein can be converted to (3R)-β-cryptoxanthin (6) and (3R,6'R)-α-cryptoxanthin (7) in a single step at room temperature, there are several major drawbacks with this process, including the use of chlorinated solvents and hydride donors such as borane-amine complexes that are not among acceptable reagents in the food industry. In addition, the process in U.S. Pat. No. 6,911,564 produced a mixture of 6 and 7 and did not yield 6 as the sole product.

Further, it was desirable to develop a process in which crude unsaponified extracts of marigold flowers containing lutein could be directly used as the starting material instead of commercially available purified lutein. Such a process could significantly reduce the cost of production of (3R)-β-cryptoxanthin and at the same time simplify the entire process.

Initial dehydration reactions were carried out with commercially available purified lutein in ethyl acetate since this solvent is one of the most commonly accepted solvents used in the food industry. The acid-catalyzed dehydration of lutein in ethyl acetate at room temperature was expected to yield anhydrolutein I (3) as the major product and anhydroluteins II (4) and III (5) as the minor products. However, it was envisioned that catalytic hydrogenation of these anhydroluteins in a one-pot reaction could be accompanied by isomerization of anhydrolutein I (3) to anhydrolutein III (5) and the latter would then undergo hydrogenation to the desired (3R)-β-cryptoxanthin (6). After conducting numerous experiments, a unique process was developed that allowed the transformation of purified lutein to (3R)-β-cryptoxanthin (6) as the major product under very mild conditions according, to the reaction sequences shown in Scheme 4. This process entailed the dehydration of lutein, transesterification, and heterogeneous catalytic hydrogenation combined into a single one-pot reaction.

In some embodiments, the heterogeneous catalyst is selected from the transition elements of group VIII. In some embodiments, the heterogeneous catalyst is platinum (Pt) supported on alumina (5%), Pt supported on activated carbon (5%), Pt supported on activated carbon (10%), palladium (Pd) supported on activated carbon (Pd/C, 5%), Pd supported on activated carbon (10%), Pd supported on alumina (5%), Pd supported on alumina (10%), Pd supported on calcium carbonate (Pd/CaCO$_3$, 5%), Pd 3% on polyethyleneimine/SiO$_2$ (Royer Pd catalyst), or rhodium (Rh) supported on alumina (5%).

With a slight modification, this process can also be applied to the direct transformation of lutein esters to (3R)-β-cryptoxanthin (6) in unsaponified extracts of marigold flower petals that is commonly referred to as marigold oleoresin. In another approach, marigold flower petals were extracted and the resulting oleoresin was, transformed into 6 according the above process.

SCHEME 4

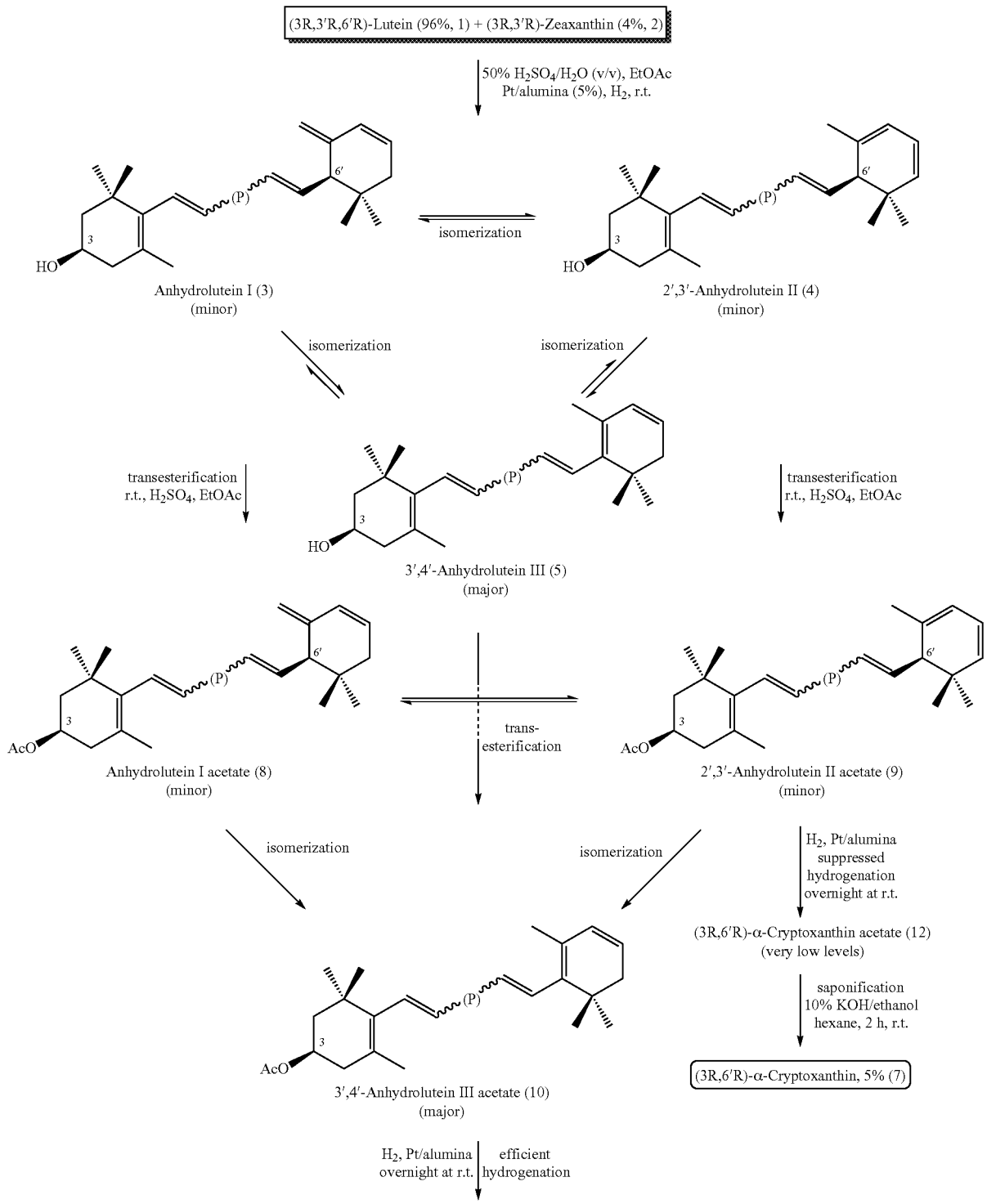

-continued

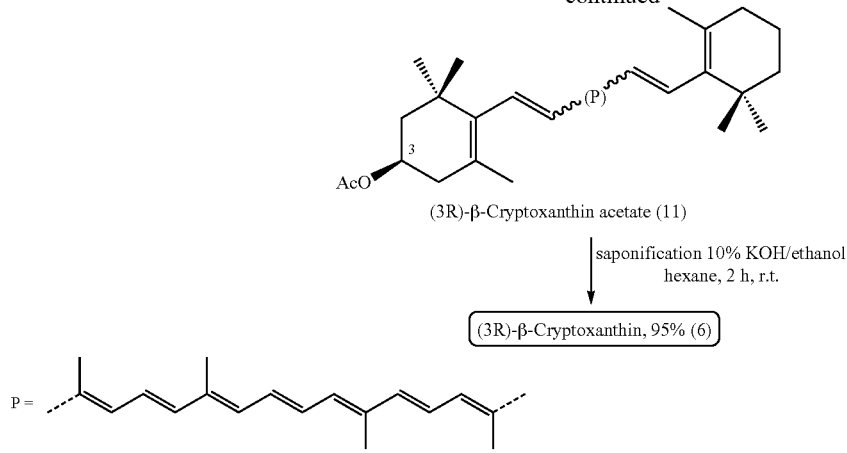

(3R)-β-Cryptoxanthin acetate (11)

↓ saponification 10% KOH/ethanol
hexane, 2 h, r.t.

(3R)-β-Cryptoxanthin, 95% (6)

P =

One-pot transformation of (3R,3'R,6'R)-lutein to (3R)-β-cryptoxanthin.

The course of the reaction was followed by high-performance liquid chromatography (HPLC). It was discovered that in this one-pot process, three types of reactions take place almost simultaneously, these were: dehydration, transesterification, and hydrogenation. In a typical experiment, a suspension of commercially available lutein (7.5 g (10 g, 75% pure), 13.19 mmol) in ethyl acetate (150 mL) in a 500 mL three-neck flask is stirred under argon or nitrogen for 15 minutes and a catalytic amount of catalyst (for example, Pt/alumina, 5% (250 mg)) is added. The mixture is cooled to 10° C. and 4 mL of 50% $H_2SO_4/H_2O$ (v/v) is added at this temperature. Upon addition of the acid, the suspension almost immediately becomes a dark red solution. The mixture is allowed to warm to ambient temperature and a stream of hydrogen is then passed 2 inches above the surface of the solution for 30 minutes and the reaction is sealed under hydrogen. Several times during the course of the reaction, the flask is filled with hydrogen and the reaction mixture is sealed under hydrogen. HPLC analysis of the reaction mixture after 4 hours, revealed that lutein is first dehydrated to a mixture of anhydroluteins I (3), II (4), and III (5) and these carotenoids subsequently undergo transesterification to form their corresponding anhydrolutein acetates I (8), II (9), and III (10) in the same ratios as their unesterified precursors. Subsequently, these carotenol acyl esters slowly undergo hydrogenation to form a mixture of (3R)-β-cryptoxanthin (6), (3R,6'R)-α-cryptoxanthin (7), (3R)-β-cryptoxanthin acetate (11), and (3R,6'R)-α-cryptoxanthin (12). The unexpectedly high ratios of 6 to 7 suggest that during hydrogenation in ethyl acetate, anhydrolutein I (3), anhydrolutein II (4) are isomerized to 3',4'-anhydrolutein III (5). Similarly, the high ratios of 11 to 12 suggests preferential isomerization of anhydrolutein I acetate (8) and 2',3'-anhydrolutein II acetate (9) to 3',4'-anhydrolutein III acetate (10). Subsequently, 5 and 10 slowly undergo hydrogenation to (3R)-β-cryptoxanthin (6) and (3R)-β-cryptoxanthin acetate (11), respectively. The dehydration of lutein to anhydroluteins and anhydrolutein acetates results in an equilibrium mixture of these carotenoids. Because 5 and 10 undergo hydrogenation preferentially in comparison to 3, 4, 8, and 9, the equilibrium in these reactions is gradually favored towards the formation of 5 and 10. As 5 and 10 are hydrogenated, 3, 4, 8, and 9 are completely isomerized to 5 and 10; the latter two carotenoids undergo catalytic hydrogenation to yield (3R)-β-cryptoxanthin (6) and (3R)-β-cryptoxanthin acetate (11) as the major product and (3R,6'R)-α-cryptoxanthin (7) and its acetate (12) as the minor product. After 24 hours, the approximate ratios of the products in the reaction mixture is: 11 (70%), 6 (25%), 7 (2%), and 12 (3%).

The mixture of these carotenoids is then subjected to saponification and crystallization to yield (3R)-β-cryptoxanthin (6) (95%) and (3R,6'R)-α-cryptoxanthin (7) (5%) in high purity. For this purpose, the product is filtered through Celite to remove the catalyst, cooled to 5-10° C., and slowly treated with 15 mL of 50% aqueous solution of NaOH (prepared from 7.5 g NaOH in 15 mL water). After stirring at room temperature for 15 minutes, ethyl acetate is distilled under reduced pressure at 30-35° C. so that saponification can be carried out. After complete removal of ethyl acetate, the residue is suspended in ethanol (50 mL) and is saponified with 15 mL of an aqueous solution of sodium hydroxide prepared from 5 g NaOH in 15 mL of water at 50-60° C. After 2 to 3 hours, the saponification is completed. The reaction mixture is allowed to cool to ambient temperature and the crystals of (3R)-β-cryptoxanthin (6) and (3R,6'R)-α-cryptoxanthin (7) are collected and washed with 30 mL of a solution of ethanol:water=3:1. At this point 6 and 7 contain substantial amounts of cis(Z)-isomers that need to be isomerized to their corresponding all-trans (all-E)-isomers. This is accomplished by suspending the crystals in a small amount of ethanol (10 mL) and heating at 50-60° C. for 3 to 4 hours in the presence of palladium diacetate [$Pd(OAc)_2$]. The reaction mixture is cooled and the crystals are collected by filtration. Recrystallization of the product from ethyl acetone and, ethanol, gives a mixture of (3R)-β-cryptoxanthin (6) (95%) and (3R,6'R)-α-cryptoxanthin (7) (5%) [5.39 g (5.5 g, 98% pure), 9.76 mmol; 74%].

In another embodiment of this invention, hydrolysis of (3R)-β-cryptoxanthin acetate (11) and (3R,6'R)-α-cryptoxanthin (12) to 6 and 7, respectively, can be accomplished by transesterification with an alcohol in the presence of catalytic amounts of an acid at an elevated temperature ranging from 60-80° C.

In another embodiment, instead of commercially available purified lutein, unsaponified extracts of marigold flower petals that are known as marigold oleoresin were used as the starting material for this transformation. As pointed out earlier, this would significantly reduce the cost of large-scale production of (3R)-β-cryptoxanthin (6) from lutein (1) and at the same time could simplify the entire process. However, this approach was extremely difficult due to the fact that lutein in unsaponified marigold extracts exists as diesters of myristic and palmitic acid. The conversion of these lutein acyl esters to their corresponding anhydrolutein esters that could serve as intermediates in heterogeneous catalytic hydrogenation to (3R)-β-cryptoxanthin (6) and (3R,6'R)-α- cryptoxanthin (7) required harsh reaction conditions. In addition, the presence of numerous impurities in crude extracts of unsaponified marigold flower petals was another problem that would make this process difficult. Furthermore, this transformation had to be carried out under mild conditions and in solvents that would be acceptable in food industry.

After conducting numerous experiments, a slight modification of the previously described process allowed the direct transformation of unsaponified crude extracts of marigold flower petals to (3R)-β-cryptoxanthin (6) and (3R,6'R)-α-cryptoxanthin (7) under very mild conditions; this process is shown in Scheme 5. According to this process, a crude ethyl acetate extract of unsaponified marigold flower petals is treated with a 50% (v/v) solution of sulfuric acid and is hydrogenation with Pt/alumina, 5% for 24-40 hours at room temperature. In the presence of acid, lutein dimyristate (13) and lutein dipalmitate (14) are first converted to a mixture of anhydrolutein III myristate (15)/palmitate (16), anhydrolutein II myristate (17)/palmitate (18), and anhydrolutein I myristate (19)/palmitate (20). Acid-catalyzed heterogeneous catalytic hydrogenation of these intermediate products results in the formation of (3R)-β-cryptoxanthin myristate (21)/palmitate (22) (98%) and (3R,6'R)-α-cryptoxanthin myristate (23)/palmitate (24) (2%). The entire process can be performed at room temperature under very mild conditions. The final step of this process involves saponification of fatty acid esters of (3R)-β-cryptoxanthin (21 & 22) and (3R,6'R)-α-cryptoxanthin (23 & 24) to yield unesterified (3R)-β-cryptoxanthin (98%) and (3R,6'R)-α-cryptoxanthin (2%). The saponification is carried out under the same conditions as described earlier for hydrolysis of (3R)-β-cryptoxanthin acetate (11) and (3R,6'R)-α-cryptoxanthin acetate (12).

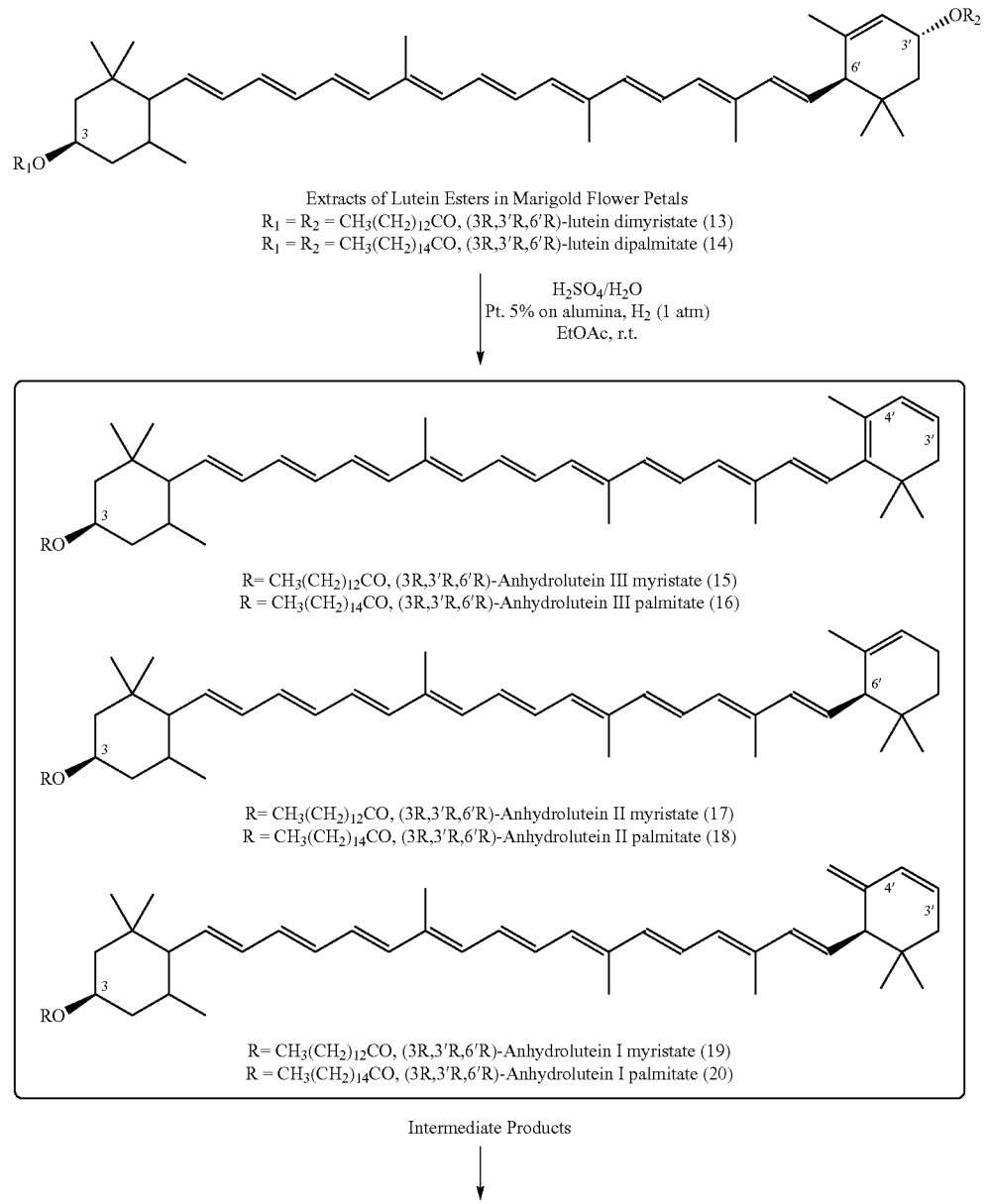

-continued

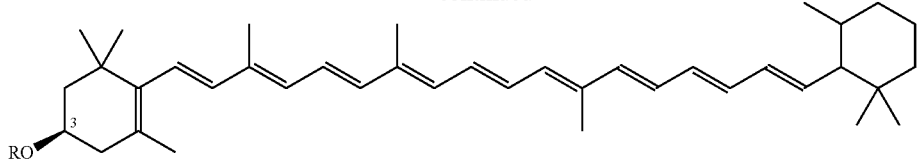

R= CH₃(CH₂)₁₂CO, (3R)-β-cryptoxanthin myristate (21)
R = CH₃(CH₂)₁₄CO, (3R)-β-cryptoxanthin palmitate (22)

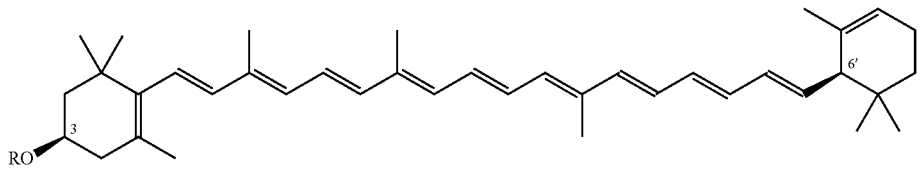

R= CH₃(CH₂)₁₂CO, (3R,6'R)-α-cryptoxanthin myristate (23)
R = CH₃(CH₂)₁₄CO, (3R,6'R)-α-cryptoxanthin palmitate (24)

| Saponification
| EtOH, NaOH
▼

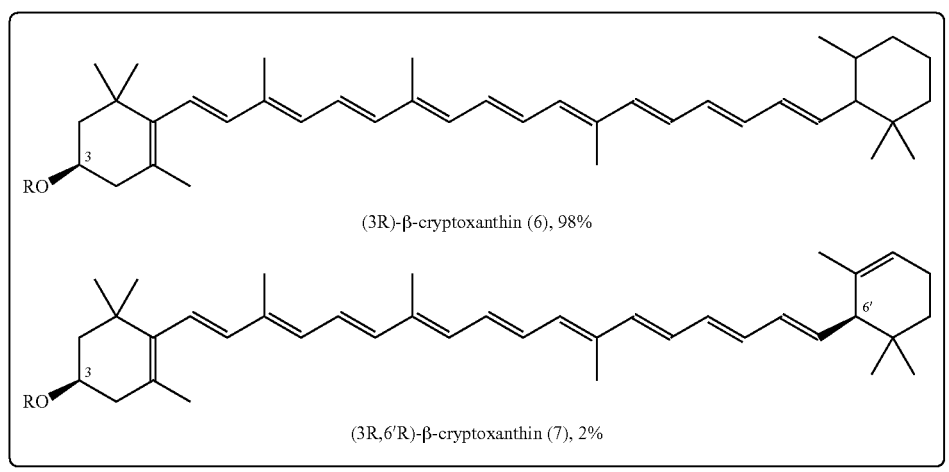

Direct transformation of extracts of Marigold flower petals containing (3R,3'R,6'R)-lutein esters to (3R)-β-cryptoxanthin and (3R,6'R)-α-cryptoxanthin.

In some embodiments, commercially available lutein (75% purity) is hydrogenated at atmospheric pressure with a heterogeneous catalyst in an acyl ester in the presence of a strong mineral acid for between about 24 to about 40 hours at room temperature.

In some embodiments, the acyl ester is methyl acetate, ethyl acetate, propyl acetate, or isopropyl acetate. In some embodiments, the acyl ester is ethyl acetate.

In some embodiments, the heterogeneous catalyst is a transition element of group VIII. In some embodiments, the heterogeneous catalyst is platinum (Pt) supported on alumina (5%), Pt supported on activated carbon (5%), Pt supported on activated carbon (10%), palladium supported on activated carbon (Pd/C, 5%), Pd supported on activated carbon (10%), Pd supported on alumina (5%), Pd supported on alumina (10%), Pd supported on calcium carbonate (Pd/CaCO₃, 5%), Pd 3% on polyethyleneimine/SiO₂ (Royer Pd catalyst), or rhodium (Rh) supported on alumina (5%). In some embodiments, the heterogeneous catalyst is Pt supported on alumina.

In some embodiments, the mineral acid is a concentrated solution of sulfuric acid, hydrochloric acid, or phosphoric acid. In some embodiments, the strong mineral acid is 50% $H_2SO_4/H_2O$ (v/v).

In some embodiments, for 10 g of lutein, the ratio of acyl ester solvent (mL):catalyst (mg):acid (mL) can be in the range of 50 (mL):80 (mg):1.5 (mL) to 150 (mL):250 (mg):4 (mL).

In some embodiments, the reaction time is between about 24 hours to about 40 hours. The reaction time is dependent on the nature of catalyst and its metal loading. This results in the formation of (3R)-β-cryptoxanthin (6) and (3R)-β-cryptoxanthin acetate (11) as the major product and (3R,6'R)-α-cryptoxanthin (7) and its acetate (12) as the minor product.

After removal of acyl ester solvent, the product is saponified with aqueous NaOH or KOH in an alcoholic solvent. In some embodiments, the alcoholic solvent is methanol, ethanol, 1-propanol, or 2-propanol. In some embodiments, the saponification occurs at temperatures between about 50° C. to about 70° C. In some embodiments, the saponification occurs for between about 30 minutes to about 24 hours. The crystalline product is then collected by filtration and the base is removed from the product by washing with an aqueous solution in a ratio of alcohol:water=3:1. At this point, the product consists of substantial amounts of cis-(3R)-β-cryptoxanthin that is converted to its all-trans isomer by catalytic isomerization with palladium diacetate [Pd(OAc)$_2$] in an alcohol at a temperature between about 50° C. to about 70° C. In some embodiments, the alcohol is ethanol. It is essential to remove the base from the product of saponification prior to isomerization with Pd(OAc)$_2$. An alternative approach to removing the base from the crystalline product consists of dissolving the product of saponification in ethyl acetate and sequentially washing, the organic layer with water, dilute acid, and saturated sodium bicarbonate.

In an alternative approach to saponification hydrolysis of (31)-β-cryptoxanthin acetate (11) and (3R,6'R)-α-cryptoxanthin (12) to 6 and 7, respectively, can be accomplished by transesterification with an alcohol in the presence of catalytic amounts of an acid at an elevated temperature of between about 60° C. to about 80° C. According to this process nearly all of the acyl ester solvent is removed under reduced pressure and the product is heated with an alcohol for between about 3 to about 4 hours to complete the hydrolysis. The hydrolysis of the cryptoxanthin esters under acidic conditions is an equilibrium that can be driven to completion as 6 and 7 precipitate and crystallize during hydrolysis. After removing the acid by washing with a mixture of alcohol:water=3:1, the isomerization of cis(Z)-cryptoxanthins to their all-trans(all-E)-isomers is carried out as follows.

A mixture of cis(Z)-cryptoxanthins and its all-trans(all-E)-isomer as a slurry in a small volume of an alcohol is heated with between about 2 to about 5 mole % of Pd(OAc)$_2$ at a temperature between about 50° C. to about 70° C. for about 2 to about 5 hours. The catalytic isomerization of this suspension results in the formation of all-E-(3R)-β-cryptoxanthin (6) as the major product (95%) and all-E-(3R,6'R)-α-cryptoxanthin (7) as the minor product (5%). The product is further crystallized from acetone and ethanol at 5° C. to yield a mixture of all-trans-6 and 7 in greater than 98% purity.

The commercially available lutein with a purity of 75% contains significant amounts of anthocyanins that can be removed prior to the above one-pot catalytic hydrogenation. Removal of the anthocyanins can be accomplished by heating a suspension of lutein in a dilute solution of an acid in an alcohol. By lowering the pH below 3, the cationic anthocyanins and degradation products of chlorophylls become soluble in alcohol and can be readily removed.

In another embodiment of the invention, commercially available lutein (10 g) is first heated with 50 mL of a 5% solution of a mineral acid (v:v), in an alcohol at a temperature between about 50° C. to about 60° C. for between about 1 and about 2 hours to remove the dark greenish anthocynins. In some embodiments, the acid is hydrochloric, sulfuric, or phosphoric acid. In some embodiments, the acid is hydrochloric acid. In some embodiments, the alcohol is methanol, ethanol, 1-propanol, or 2-propanol. After removal of the solution of acidic alcohol by filtration or centrifugation, lutein crystals are washed with 10 mL of an alcohol and used directly in the above process. During this initial treatment, lutein undergoes dehydration to form anhydroluteins I, II, and III without any loss or degradation due to the fact that temperature is maintained below 60° C.

In another embodiment of this invention, an extract of marigold flower petals can be used as the starting material for direct transformation of lutein esters to predominantly all-E-(3R)-β-cryptoxanthin (6) according to Scheme 5. In a typical experiment, marigold petals (20 g) are extracted with a food grade organic solvent, wherein the food grade organic solvent is ethyl acetate, methyl acetate, isopropyl acetate (150 mL), acetone, or ethers. In some embodiments, the ether is diethyl ether, diisopropyl ether, tert-butyl methyl ether, or tetrahydrofuran. After solvent evaporation, approximately 3.0 g of an oleoresin is obtained that has a carotenoid content of about 0.42 g. This corresponds to a total carotenoid content of 2%. Most commercially available marigold oleoresins have approximately 2 to 3% total carotenoid content. Therefore in an alternative embodiment of this process, 6 g of marigold oleoresin is heated with a 5% solution of HCl in an alcohol (v:v), wherein in some embodiments, the alcohol is methanol, ethanol, 1-propanol, or 2-propanol, at between about 50° C. to about 60° C. for about 1 to about 2 hours to remove the dark greenish anthocycnins and the degradation products of chlorophylls. The residue is then dissolved in an acyl ester solvent and is subjected to heterogeneous catalytic hydrogenation in the presence of 1 mL of a 50% solution of an acid and a heterogeneous catalyst for about 24 hours. In some embodiments, the acyl ester solvent is ethyl acetate. In some embodiments, the acid is $H_2SO_4/H_2O$ (v:v). In some embodiments, the heterogeneous catalyst is Pt/alumina. The acyl ester solvents, the catalyst and the mineral acid can be the same as those described in the earlier process for transformation of purified lutein to (3R)-β-cryptoxanthin (6).

The saponification/hydrolysis and its work up, isomerization of cis(Z)-β-cryptoxanthin to all-trans (all-E), and purification process for isolation of 6 is carried out under the same conditions as previously described. The main advantage of this process is the fact that only one saponification is needed as opposed to the process developed for the transformation of purified lutein to 6. This is because to obtain purified lutein, the extracts of marigold flower petals are first saponified and the transformation of the purified lutein to 6 requires a second saponification. In addition, this process significantly reduces the cost for large-scale production of 6.

It will be readily apparent to one of ordinary skill in the relevant art that other suitable modifications and adaptations to the process and applications described herein are obvious and may be made without departing from the scope of the invention or any embodiment thereof. Having now described the present invention in detail, the same will more clearly be understood by reference to the following examples, which are included herewith for purposes of illustration only and are not intended to be limiting of the invention.

EXPERIMENTAL

Reagents and Starting Materials

Three, types of starting materials were employed as the source of (3R,3'R,6'R)-lutein according to this invention, these were (1) commercially available (3R,3'R,6'R)-lutein with the purity of approximately 75% total carotenoid; (2) commercially available marigold oleoresin that contained lutein fatty acid esters; and (3) commercially available marigold petals that were extracted to obtain marigold oleoresin. All starting materials were from extraction of marigold flower petals and contained approximately 5-7% (3R,3'R)-zeaxanthin. Acyl ester solvents, alcohols, concentrated mineral acids, and heterogeneous catalysts for hydrogenation, and Celite (diatomaceous earth or filter aid) were all obtained from Sigma-Aldrich.

Example 1

Conversion of Commercially Available Lutein to (3R)-β-Cryptoxanthin

A suspension of commercially available (3R,3'R,6'R)-lutein (10 g of 75% pure 7.5 g, 13.19 mmol) in ethyl acetate (150 mL) in a 500 mL 3-neck flask equipped with a gas inlet and a thermometer was stirred under nitrogen for 10 minutes. The flask was cooled to 10° C. and the mixture was treated with slow addition of 4.0 mL of a 50% aqueous solution of sulfuric acid (v:v, prepared from 2 mL of concentrated $H_2SO_4$ and 2 mL of water) in 10 minutes. The reaction mixture was allowed to warm to room temperature. Almost immediately, the suspension became a dark red solution. To the stirred solution was added platinum on alumina, 5% (250 mg) and a stream of hydrogen was passed 2 inches above the surface of the solution for 30 minutes. The reaction mixture was then sealed under hydrogen and was allowed to stir at room temperature for nearly 24 hours. At two intervals during the reaction, after 4 and 8 hours, hydrogen was passed above the reaction mixture and the flask was sealed under hydrogen. After 24 hours, HPLC showed the complete conversion of lutein to (3R)-β-cryptoxanthin (6) and (3R)-β-cryptoxanthin acetate (11) that were accompanied by minor amounts of (3R,6'R)-α-cryptoxanthin (7) and (3R,6'R)-α-cryptoxanthin acetate (12). The product was filtered through Celite (diatomaceous earth or filter aid) to remove the catalyst. The Celite was washed with ethyl acetate until colorless. The hydrolysis of 11 and 12 in the mixture of products was carried out by two different processes, these were: saponification and transesterification as described below.

Process A

Saponification of (3R)-β-cryptoxanthin acetate (11) and (3R,6'R)-α-cryptoxanthin acetate (12)

The above solution of cryptoxanthin acetates was cooled down to 5-10° C., and was slowly treated with 15 mL of 50% aqueous solution of NaOH (prepared from 7.5 g NaOH in 15 mL water). After stirring at room temperature for 15 minutes, ethyl acetate was removed under reduced pressure at 30-40° C. so that saponification could be carried out. After complete removal of ethyl acetate, the residue was suspended in ethanol (50 mL) and was treated with a 15 mL aqueous solution of sodium hydroxide (prepared from 5 g NaOH in 15 mL of water). The suspension was heated at 50-60° C. for 2 to 3 hours to complete the saponification. The reaction mixture was allowed to cool to ambient temperature and the crystals of (3R)-β-cryptoxanthin (6) and (3R,6'R)-α-cryptoxanthin (7) were collected by filtration and washed twice with 2×30 mL solution of ethanol:water=3:1 to remove the base. Alternatively, the product was dissolved in ethyl acetate and sequentially washed with water, 5% aqueous solution of HCl, and saturated sodium bicarbonate to remove the base. After solvent evaporation under reduced pressure, 6 and 7 were obtained as orange, crystals. The crystals were suspended in 10 mL of ethanol, 50 mg of $Pd(OAc)_2$ was added, and the mixture was heated at 50-60° C. for 3 to 4 hours to isomerize (cis)Z-cryptoxanthins to their all-trans (all-E)-isomers. The reaction mixture was cooled to 5° C. and the crystals were collected by filtration. The product was then further purified by crystallization from acetone (10 mL) and ethanol (30 mL) to give a mixture of (3R)-β-cryptoxanthin (6) (95%) and (3R,6'R)-α-cryptoxanthin (7) (5%) [5.39 g (5.5 g, 98% pure), 9.76 mmol; 74%].

Process B

Transesterification of (3R)-β-cryptoxanthin acetate (11) and (3R,6'R)-α-cryptoxanthin acetate (12)

After removal of the catalyst, by filtration in example 1, most of the ethyl acetate was evaporated until only 10 to 15 mL of the solvent remained in the flask. Ethanol (30 mL) was added and the mixture was heated at temperatures between 60-80° C. for 2 hours to complete the conversion of 11 and 12 to 6 and 7, respectively. The product was then partitioned between water (40 mL) and ethyl acetate (40 mL) to remove the acid. The water layer was removed and the organic layer was washed with saturated sodium bicarbonate (40 mL) and evaporated to dryness. The residue was then subjected to catalytic isomerization with $Pd(OAc)_2$ and purified by crystallization as described above to yield a mixture of (3R)-β-cryptoxanthin (6) (95%) and (3R,6'R)-α-cryptoxanthin (7) (5%) [4.90 g (5.0 g, 98% pure), 8.89 mmol; 67%)].

Example 2

Conversion of Lutein Esters in an Unsaponified Extract of Marigold Oleoresin to (3R)-β-Cryptoxanthin An unsaponified extract of marigold oleoresin (6 g) in a 100 mL 3-neck flask equipped with a gas inlet and a thermometer was treated with 50 mL of a 5% solution of hydrochloric acid in ethanol (v:v) and the mixture was heated at 50-60° C. for 1-2 hours to remove the dark greenish anthocyanins and degradation products of chlorophylls. The solution was removed by decantation and the remaining dark red paste was washed with 10 mL of ethanol and the alcohol was decanted. This pre-treatment of the marigold oleoresin resulted in the removal of 1.3 g of anthocyanins from the oleoresin. The dark red paste was dissolved in ethyl acetate (30 mL) and stirred under nitrogen for 10 min. Pt/alumina, 5% (50 mg) was added followed by slow addition of a 50% (v/v) solution of sulfuric acid (1 mL). A stream of hydrogen was then passed 2 inches above the surface of the solution for 30 minutes and the reaction flask was sealed under hydrogen. At two intervals during the reaction, after 4 and 8 hours, hydrogen was passed above the reaction mixture and the flask was sealed under hydrogen. After 24 hours, the product was filtered through Celite (filter aid) and the Celite was washed with ethyl acetate until it was colorless. The filtrate was transferred into a separatory funnel and the organic layer was washed sequentially with water and saturated $NaHCO_3$ and evaporated to dryness. The residue was suspended in 20 mL of ethanol and an aqueous solution of NaOH (1 g) in 3 mL of water. The mixture was heated at 50-60° C. for 2 hours to complete the saponification. The mixture was then partitioned between water (30 mL) and ethyl acetate (30 mL). The aqueous layer was removed and the organic layer was sequentially washed with 5% aqueous solution of HCl (20 mL), and saturated sodium bicarbonate (20 mL) to remove the base. After solvent evaporation under reduced pressure, 6 and 7 were obtained as orange crystals. The crystals were suspended in 5 mL of ethanol, 5 mg of Pd(OAC)$_2$ was added, and the mixture was heated at 50-60° C. for 3 to 4 hours to isomerize (cis)Z-cryptoxanthins to their all-trans (all-E)-isomers. The reaction mixture was cooled to 5° C. and the crystals were collected by filtration. The product was then further purified by crystallization from acetone (5 mL) and ethanol (15 mL) to give a mixture of (3R)-β-cryptoxanthin (6) (98%) and (3R,6'R)-α-cryptoxanthin (7) (2%) [0.59 g (0.60 g, 98% pure), 1.07 mmol].

Example 3

Conversion of Lutein Esters in an Extract from Marigold Flower Petals to (3R)-β-Cryptoxanthin Marigold flower petals (22 g) were transferred into a homogenizer and extracted with 200 mL of ethyl acetate at room temperature for 2 h. The dark red extract was filtered through Celite (filter aid) and the Celite was washed with 50 mL of ethyl acetate until it was colorless. The filtrate was transferred into a round bottom flask and most of the ethyl acetate was distilled under reduced pressure at 30-40° C. to dryness to give 3.2 g of an oleoresin. The total carotenoid content of this oleoresin measured by UV-Visible spectrophotometry was 0.416 g of lutein fatty acid esters. The oleoresin was transferred into a 100 mL 3 neck flask using 30 mL of ethyl acetate. Pt/alumina, 5% (25 mg) was added followed by slow addition of a 50% (v/v) solution of sulfuric acid (0.5 mL). A stream of hydrogen was then passed 2 inches above the surface of the solution for 30 minutes and the reaction flask was sealed under hydrogen. At two intervals during the reaction, after 4 and 8 hours, hydrogen was, passed above the reaction mixture and the flask was sealed under hydrogen. After 24 hours, the product was filtered through Celite (filter aid) and the Celite was washed with ethyl acetate until it was colorless. The filtrate was transferred into a separatory funnel and, the organic layer was washed sequentially with water, saturated NaHCO$_3$ and evaporated to dryness. The residue was suspended in 10 mL of ethanol and an aqueous solution of NaOH (0.5 g) in 1 mL of water. The mixture was heated at 50-60° C. for 2 hours to complete the saponification. The mixture was then partitioned between water (15 mL) and ethyl acetate (15 mL). The aqueous layer was removed and the organic layer was sequentially washed with 5% aqueous solution of HCl (10 mL), and saturated sodium bicarbonate (10 mL) to remove the base. After solvent evaporation under reduced pressure, 6 and 7 were obtained as orange crystals. The crystals were suspended in 3 mL of ethanol, 2 mg of Pd(OAc)$_2$ was added and the mixture was heated at 50-60° C. for 3 to 4 hours to isomerize (cis)Z-cryptoxanthins to their all-trans (all-E)-isomers. The reaction mixture was cooled to 5° C. and the crystals were collected by filtration. The product was then further purified by crystallization from acetone (3 mL) and ethanol (10 mL) to give a mixture of (3R)-β-cryptoxanthin (6) (98%) and (3R,6'R)-α-cryptoxanthin (7) (2%) [0.29 g (0.30 g, 98% pure), 0.53 mmol].

Having no fully described this invention, it will be understood by those of ordinary skill in the art that the same can be performed within a wide and equivalent range of conditions, formulations and other parameters without affecting the scope of the invention or any embodiment thereof. All patents, patent applications, and publications cited herein are fully incorporated by reference herein in their entirety.

What is claimed is:

1. A process for the preparation of (3R)-β-cryptoxanthin acetate comprising reacting (3R,3'R,6'R)-lutein with concentrated mineral acid or a strong organic acid, a heterogeneous hydrogenation catalyst, an acylating ester, and hydrogen in one reaction to give (3R)-β-cryptoxanthin acetate.

2. The process of claim 1, wherein the (3R,3'R,6'R)-lutein is purified by pretreatment with a dilute solution of a mineral acid in an alcohol at a temperature between about 50° C. to about 60° C. to remove anthocyanins and degradation products of chlorophylls.

3. The process of claim 1, further comprising a solvent selected from the group consisting of acetone, tetrahydrofuran, a hydrocarbon solvent, and combinations thereof.

4. The process of claim 1, wherein the acylating ester is selected from the group consisting of ethyl acetate, methyl acetate, isopropyl acetate, propyl acetate, and isopropenyl acetate.

5. The process of claim 3, wherein the hydrocarbon solvent is selected from the group consisting of pentane, hexane, and heptane.

6. The process of claim 1, wherein the concentrated mineral acid or strong organic acid is selected from the group consisting of about 50% sulfuric acid, hydrochloric acid, phosphoric acid, trifluoroacetic acid, and benzenesulfonic acid.

7. The process according to claim 1, wherein the heterogeneous hydrogenation catalyst is selected from the group consisting of platinum (Pt) supported on alumina (5%), Pt supported on activated carbon (5%), Pt supported on activated carbon (10%), palladium (Pd) supported on activated carbon (5%), Pd supported on activated carbon (10%), Pd supported on alumina (5%), Pd supported on alumina (10%), Pd supported on calcium carbonate (5%), Pd 3% on polyethyleneimine/SiO$_2$, rhodium (Rh) supported on alumina (5%), ruthenium supported on carbon, and ruthenium supported on alumina.

8. The process according to claim 1, wherein the reacting is carried out at a temperature between about 23° C. to about 45° C.

9. The process of claim 1, wherein the (3R,3'R,6'R)-lutein is present in a composition comprising 4-5% (3R,3'R)-zeaxanthin.

10. The process of claim 1, wherein the (3R,3'R,6'R)-lutein may be present as lutein fatty acid esters in a composition comprising 4-5% (3R,3'R)-zeaxanthin fatty acid esters.

11. The process of claim 10, wherein the lutein fatty acid esters are selected from the group consisting of lutein dimyristate, lutein dipalmitate, and combinations thereof.

12. The process of claim 10, wherein the source of the lutein fatty acid esters is extracts of marigold flowers or marigold petal flowers.

13. The process of claim 10, wherein the lutein fatty acid esters are purified by pretreatment with a dilute solution of a mineral acid in an alcohol at a temperature between about 50° C. and about 60° C. to remove the anthocyanins and degradation products of chlorophylls.

14. The process of claim 13, wherein the mineral acid is selected from the group consisting of hydrochloric acid, sulfuric acid, and phosphoric acid.

* * * * *